United States Patent
Kim et al.

(10) Patent No.: US 11,673,948 B2
(45) Date of Patent: Jun. 13, 2023

(54) ANTI-TNF/IFN SCFV-FC BISPECIFIC ANTIBODY AND USES THEREOF

(71) Applicant: JP DUETBIO CO., LTD, Seoul (KR)

(72) Inventors: Dong-Il Kim, Incheon (KR);
Hyun-Myoung Cha, Seoul (KR);
Jin-Hyuk Lim, Seoul (KR)

(73) Assignee: JP DUETBIO CO., LTD, Seoul (KR)

( * ) Notice: Subject to any disclaimer, the term of this patent is extended or adjusted under 35 U.S.C. 154(b) by 252 days.

(21) Appl. No.: 17/115,163

(22) Filed: Dec. 8, 2020

(65) Prior Publication Data

US 2022/0177571 A1   Jun. 9, 2022

(51) Int. Cl.
*C07K 16/24* (2006.01)

(52) U.S. Cl.
CPC .......... *C07K 16/249* (2013.01); *C07K 16/241* (2013.01); *C07K 2317/31* (2013.01); *C07K 2317/52* (2013.01); *C07K 2317/622* (2013.01)

(58) Field of Classification Search
None
See application file for complete search history.

(56) References Cited

FOREIGN PATENT DOCUMENTS

KR   10-2019-0143070 A   12/2019

OTHER PUBLICATIONS

Shivashankar et al. 'Mimics of Inflammatory Bowel Disease.' Inflamm Bowel Dis • vol. 24, No. 11, 2315-2321, 2018.*

* cited by examiner

*Primary Examiner* — Nora M Rooney
(74) *Attorney, Agent, or Firm* — Sughrue Mion, PLLC

(57) ABSTRACT

Disclosed is anti-TNF/IFN scFv-Fc bispecific antibody and a pharmaceutical composition for prevention or treatment of inflammatory bowel disease, the composition containing the antibody. The bispecific antibody has a structure in which an Fc fragment is conjugated to an scFv bispecific antibody. Thus, a purification process thereof may be easy. The bispecific antibody may effectively and simultaneously conjugate to TNF-α and IFN-γ which independently play an important role in inducing Crohn's disease. Thus, the bispecific antibody may exhibit excellent effects in the treatment of inflammatory bowel disease including Crohn's disease.

17 Claims, 8 Drawing Sheets

Specification includes a Sequence Listing.

US 11,673,948 B2

ANTI-TNF/IFN SCFV-FC BISPECIFIC ANTIBODY AND USES THEREOF

TECHNICAL FIELD

The present disclosure relates to anti-TNF/IFN scFv-Fc bispecific antibody and a pharmaceutical composition for prevention or treatment of inflammatory bowel disease, the composition containing the antibody.

BACKGROUND

In general, in an antibody, a heterodimer is formed by linking polypeptides of a heavy chain with a large molecular weight and a light chain with a small molecular weight to each other via a disulfide bond, and then, two heterodimers are connected to each other via a disulfide bond to form a tetramer. The polypeptide that constitutes the heavy chain is composed of four domains consisting of a variable domain, a constant domain 1, a constant domain 2, and a constant domain 3 in this order from an N-terminus thereof. The polypeptide that constitutes the light chain is composed of two domains containing a variable domain and a constant domain in this order from an N-terminus thereof. A conjugate of the variable domain of the heavy chain and the variable domain of the light chain is conjugated with one antigen.

An antigen-antibody binding reaction of the antibody exhibited high specificity, and an antigenic site that interacts with the antibody is referred to as an antigenic determinant or epitope. The antigenic determinant is specifically conjugated to the variable domain as the antigen-binding site of the antibody. Since the antigen-binding site may be conjugated with only one antigenic determinant, each of numerous antibodies may provide unique immunity to each of antigens having each specific determinant.

Further, there is a bispecific antibody capable of recognizing two types of antigens. The bispecific antibody is prepared by modifying the antibody using recombinant DNA technology to have two antigen-binding sites capable of binding to two different antigens, respectively. Alternatively, the bispecific antibody is prepared as a two-in-one antibody as a normal antibody having one antigen-binding site which has the ability to bind to two different antigens (Bostrom, J et. al., Science 323, 1610-1614, 2009). In the bispecific antibody prepared by the former method, a first binding site may be specific to a specific antigen, while a second binding site may be specific to another antigen. Thus, the bispecific antibody may be conjugated with two antigens simultaneously (Beck A et. al., Nat Rev immunology 10; 345-352, 2010). The bispecific antibody prepared by the latter method may be a normal antibody having one antigen-binding site and have the ability to bind to two different antigens. Since this two-in-one antibody has one antigen-binding site, the antibody may conjugate with one antigen at a time rather than conjugate with two antigens at the same time and may have the ability to bind to two different antigens. The bispecific antibody may have the advantage of high target specificity because the antibody may bind to specific toxic cells and target cells.

Inflammatory bowel disease including Crohn's disease and ulcerative colitis is a chronic disease, and an important cause of the inflammatory bowel disease is immune response regulatory abnormalities. Recently, as cytokines or cells related to inflammatory bowel disease have been identified via active research on the inflammatory bowel disease, a number of studies on biological agents that selectively attack specific molecules or pathways related to intestinal inflammation have been conducted. Biological agents that may be considered in inflammatory bowel disease may include inflammatory cytokine inhibitors containing anti-tumor necrosis factor (anti-TNF) agents, anti-inflammatory cytokines, cell adhesion inhibitors, T cell activation inhibitors, immunostimulants, gene therapy, and mitogen-activated protein kinase (MAPK) inhibitors depending on their mechanism of action. Anti-TNF agents were the first biological agents which were used for the treatment of inflammatory bowel disease. Among them, infliximab and adalimumab were approved for Crohn's disease, and infliximab was approved for ulcerative colitis.

However, ⅓ of patients have no response to these anti-TNF agents, and experience a decrease in treatment response due to antibody formation. Further, serious side effects such as infection or malignant lymphoma have been reported. Therefore, there is a need to develop new agents that may treat inflammatory bowel diseases such as Crohn's disease.

SUMMARY

Therefore, while the present inventors have researched a new agent that may treat inflammatory bowel diseases such as Crohn's disease, we have identified that targeting TNF-α and IFN-γ independently acting on Crohn's disease at the same time allows excellent Crohn's disease treatment effect. Thus, the present disclosure was completed.

Therefore, the present disclosure provides a polynucleotide encoding a bispecific antibody having binding specificity to TNF-α and IFN-γ, the polynucleotide containing anti-TNF scFv-Fc represented by SEQ ID NO: 1 and anti-IFN scFv-Fc represented by SEQ ID NO: 2. The present disclosure provides a preparation method of the bispecific antibody and a pharmaceutical composition for the prevention or treatment of inflammatory bowel disease, the composition containing the bispecific antibody.

One aspect of the present disclosure provides a polynucleotide encoding a bispecific antibody having binding specificity to TNF-α and IFN-γ, the polynucleotide containing anti-TNF scFv-Fc represented by SEQ ID NO: 1 and anti-IFN scFv-Fc represented by SEQ ID NO: 2.

Further, another aspect of the present disclosure provides a bispecific antibody having binding specificity to TNF-α and IFN-γ, the bispecific antibody containing anti-TNF scFv-Fc represented by SEQ ID NO: 3 and anti-IFN scFv-Fc represented by SEQ ID NO: 4.

Further, still another aspect of the present disclosure provides a recombinant expression vector containing the polynucleotide.

Further, still another aspect of the present disclosure provides a host cell transformed using the vector.

Further, still another aspect of the present disclosure provides a method for preparing a bispecific antibody having binding specificity to TNF-α and IFN-γ, the method including 1) preparing a transformant by introducing anti-TNF scFv-Fc represented by SEQ ID NO: 1 and anti-IFN scFv-Fc represented by SEQ ID NO: 2 into host cells, and 2) culturing the transformant in a medium and separating and purifying an anti-TNF/IFN scFv-Fc bispecific antibody expressed in the medium.

Further, still another aspect of the present disclosure provides a bispecific antibody prepared by the above preparation method.

Further, still another aspect of the present disclosure provides a pharmaceutical composition for the prevention or treatment of inflammatory bowel disease, the composition containing the bispecific antibody.

According to the above aspects of the present disclosure, the bispecific antibody having binding specificity to TNF-α and IFN-γ according to the present disclosure has a structure in which an Fc fragment is conjugated to an scFv bispecific antibody. Thus, the purification process thereof may be easy. The bispecific antibody may effectively and simultaneously conjugate to TNF-α and IFN-γ which independently play an important role in inducing Crohn's disease. Thus, the bispecific antibody may exhibit excellent effects in the treatment of inflammatory bowel disease including Crohn's disease.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
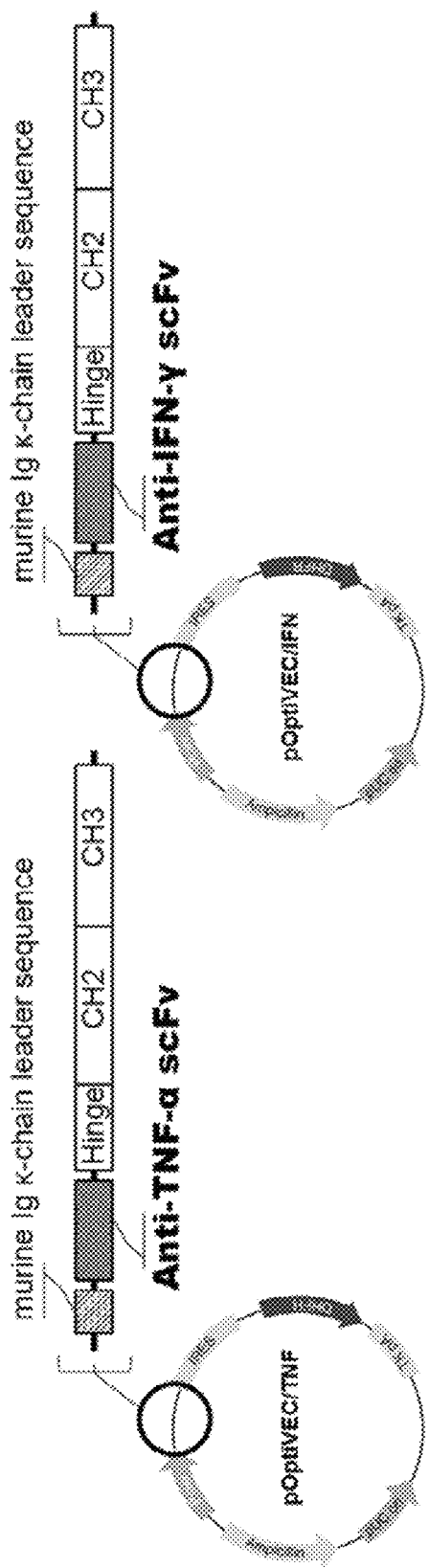
FIG. 1 is a diagram showing expression vectors for preparing anti-TNF-α scFv and anti-IFN-γ scFv used for transformation into a CHO-DG44 cell line.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented herein.

The present disclosure relates to a polynucleotide encoding a bispecific antibody having binding specificity to TNF-α and IFN-γ, the polynucleotide containing anti-TNF scFv-Fc represented by SEQ ID NO: 1 and anti-IFN scFv-Fc represented by SEQ ID NO: 2.

Further, the present disclosure relates to a bispecific antibody having binding specificity to TNF-α and IFN-γ, the bispecific antibody containing anti-TNF scFv-Fc represented by SEQ ID NO: 3 and anti-IFN scFv-Fc represented by SEQ ID NO: 4.

The bispecific antibody having binding specificity to TNF-α and IFN-γ according to the present disclosure may be easily and quickly purified via fusion of the Fc fragment, and may exhibit excellent binding ability to both TNF-α and IFN-γ as cytokines that cause inflammatory bowel disease including Crohn's disease. Thus, the bispecific antibody may be used as a new therapeutic agent for inflammatory bowel disease.

The bispecific antibody having binding specificity to TNF-α and IFN-γ according to the present disclosure has a structure in which an Fc fragment is conjugated to an scFv bispecific antibody. Thus, the antibody may be easily purified using the Fc fragment, thereby to increase a half-life thereof.

The polynucleotide encoding the bispecific antibody having binding specificity to TNF-α and IFN-γ and containing anti-TNF scFv-Fc represented by SEQ ID NO: 1 and anti-IFN scFv-Fc represented by SEQ ID NO: 2 is a codon optimized gene for expression in mammalian cell lines. The polynucleotide may include a sequence having a homology of 60% or more, preferably 75% or more, more preferably 95% or more thereto, as long as the functional properties of the amino acid encoded by the sequence are not substantially changed.

Further, the present disclosure provides a bispecific antibody having binding specificity to TNF-α and IFN-γ, the antibody containing anti-TNF scFv-Fc represented by SEQ ID NO: 3 and anti-IFN scFv-Fc represented by SEQ ID NO: 4.

Further, as long as the characteristics of the antibody according to the present disclosure are maintained, a variant thereof in which mutation occurs within a variable domain thereof is included within the scope of rights of the present disclosure. One example of the variant may result from the conservative substitution of amino acid in the variable domain. The conservative substitution refers to substitution of an original amino acid sequence with other amino acid residues having properties similar to those of the original amino acid sequence. For example, lysine, arginine, and histidine have base side chains and thus have similar properties. Aspartic acid and glutamic acid have similar properties in that they have acid side chains. Further, glycine, asparagine, glutamine, serine, threonine, tyrosine, cysteine and tryptophan have similar properties in that they have a non-charged polar side chain. Alanine, valine, leucine, threonine, isoleucine, proline, phenylalanine, and methionine have similar properties in that they have non-polar side chains. Tyrosine, phenylalanine, tryptophan, and histidine have aromatic side chains and thus have similar properties. Therefore, it is obvious to a person skilled in the art that even when an amino acid substitution occurs in the same group having similar characteristics as described above, any change in characteristics thereof does not occur. As long as the characteristics of the antibody according to the present disclosure are maintained, antibodies in which mutation occurs via conservative substitution within the variable domain are also included in the scope of rights according to the present disclosure.

Further, the present disclosure provides a polynucleotide encoding a bispecific antibody having binding specificity to TNF-α and IFN-γ. That is, the polynucleotide encodes the bispecific antibody having binding specificity to TNF-α and IFN-γ. That is, a sequence may be included in the polynucleotide according to the present disclosure without limitation, as long as the sequence is capable of producing a bispecific antibody having the binding specificity to TNF-α and IFN-γ and containing anti-TNF scFv-Fc represented by SEQ ID NO: 3 and anti-IFN scFv-Fc represented by SEQ ID NO: 4 as desired when the sequence is translated into protein. Preferably, the polynucleotide may be represented by SEQ ID NO: 1 and SEQ ID NO: 2.

The present disclosure further provides a recombinant expression vector containing the polynucleotide and a host cell transformed using the vector.

In the present disclosure, the term "recombinant expression vector" is an expression vector capable of expressing a target protein in a suitable host cell, and refers to a genetic construct containing an essential regulatory element operably linked to allow a gene insert to be expressed. In the present disclosure, the term "operably linked" refers to a functional link between a nucleic acid expression control sequence and a nucleic acid sequence encoding a protein of interest to perform a general function. The operative linkage with the recombinant vector may be made using gene recombination technology well known in the technical field to which the present disclosure belongs. Site-specific DNA cleavage and ligation may be easily performed using enzymes generally known in the art to which the present disclosure belongs.

Suitable expression vectors that may be used in the present disclosure may include not only expression regulatory elements such as promoters, initiation codons, termination codons, polyadenylation signals and enhancers, but also signal sequences for membrane targeting or secretion. The initiation and termination codons are generally considered to be a portion of the nucleotide sequence encoding the immunogenic target protein. When the genetic construct is administered to the subject, the initiation and termination codons must exhibit an action in the subject and must be in frame with a coding sequence. Generic promoters may be constitutive or inducible.

The expression vector may contain a selection marker for selecting a host cell containing the vector. The selection marker is configured for selecting cells transformed using the vector, and may include markers that provides a selectable phenotype such as drug resistance, auxotrophy, resistance to cytotoxicity agents or expression of surface proteins. Since only cells expressing the selection marker survive in an environment treated with a selective agent, transformed cells may be selected. Further, when the vector is a replicable expression vector, the vector may contain a replication origin as a specific nucleic acid sequence at which replication is initiated. The recombinant expression vector may include various types of vectors such as plasmids, viruses, and cosmids. The type of the recombinant vector is not particularly limited as long as it has a function of expressing a desired gene and producing a desired protein in various host cells such as prokaryotic and eukaryotic cells. However, a vector capable of mass-producing a foreign protein in a form similar to a form of a natural state while retaining strong expression power with a strong active promoter is preferable.

Various expression host/vector combinations may be used to express the antibody or the antibody fragment according to the present disclosure. Expression vectors suitable for the eukaryotic host may include, but are not limited to, expression regulatory sequences and the like derived from SV40, bovine papillomavirus, anenovirus, adeno-associated virus, cytomegalovirus, and retrovirus. In the present disclosure, the pOptiVEC-TOPO vector was used as a preferred example thereof.

The recombinant vector is inserted into a host cell to form a transformant. Suitable host cells may be eukaryotic cells such as animal cells, plant cells, yeast, E. coli, and insect cells. Further, the host cell may preferably be derived from a plant or mammal. The host cell may include monkey kidney cells (COS7) cell, NSO cell, SP2/0, Chinese hamster ovary (CHO) cell, W138, baby hamster kidney (BHK) cell, MDCK, myeloma cell line, HuT 78 cell, HEK293 cell, and the like. Preferably, the host cell may be a CHO cell, but is not limited thereto.

More specifically, the bispecific antibody according to the present disclosure may be prepared by a method including 1) preparing a transformant by introducing anti-TNF scFv-Fc represented by SEQ ID NO: 1 and anti-IFN scFv-Fc represented by SEQ ID NO: 2 into host cells, and 2) culturing the transformant in a medium and separating and purifying an anti-TNF/IFN scFv-Fc bispecific antibody expressed in the medium.

In the step 1), the transformant is prepared via transformation into the host cell. In the present disclosure, the term "transformation into a host cell" may be performed by a method known in the art for introducing a nucleic acid into an organism, cell, tissue or organ. For example, the method may include electroporation, protoplasm fusion, calcium phosphate ($CaPO_4$) precipitation, calcium chloride ($CaCl_2$) precipitation, agitation using silicon carbide fibers, agrobacterial-mediated transformation, PEG, dextran sulfate, lipofectamine, drying/inhibition-mediated transformation methods, and the like. However, the present disclosure is not limited thereto.

In the step 2), the transformant expressing the recombinant vector is cultured in a nutrient medium to produce many bispecific antibodies having binding specificity to TNF-α and IFN-γ according to the present disclosure. The medium and culture conditions may be appropriately selected and used based on the host cell. During cultivation, conditions such as temperature, pH of the medium, and culture time may be appropriately adjusted to be suitable for the growth of cells and mass production of proteins. The antibody or antibody fragment as produced recombinantly as described above may be recovered from a medium or cell digest product. The separation and purification thereof may be made by conventional biochemical separation techniques.

The separation and purification step in the step 2) may include electrophoresis, centrifugation, gel filtration, precipitation, dialysis, chromatography (ion exchange chromatography, affinity chromatography, immunosorbent chromatography, size exclusion chromatography, etc.), isoelectric point focusing and various modified and complex methods thereof, but are not limited thereto. In particular, considering that the antibody of the present invention is in a form in which the Fc fragment is fused thereto, it is preferable to perform the step while targeting the Fc domain. More preferably, the separation and purification may be performed using Protein A.

The present disclosure provides a bispecific antibody having binding specificity to TNF-α and IFN-γ, the antibody being prepared by the above preparation method.

The bispecific antibody is composed of an amino acid sequence translated using the nucleotide represented by SEQ ID NO: 1 and SEQ ID NO: 2. The bispecific antibody has binding specificity to TNF-α and IFN-γ, and contains anti-TNF scFv-Fc represented by SEQ ID NO: 3 and anti-IFN scFv-Fc represented by SEQ ID NO: 4. The addition, deletion or substitution of one or more amino acids thereof may be made while not substantially changing the functional properties of the antibody.

Further, the antibody or fragment thereof according to the present disclosure may be used in the form of a conjugate in which the antibody or fragment thereof is conjugated to another substance. Examples of the substance binding to the antibody or fragment thereof according to the present disclosure may include antibodies for treating inflammatory bowel disease, and conventional treatment agents for inflammatory bowel diseases such as antihistamines or anti-inflammatory drugs, but are not limited thereto.

Further, the present disclosure provides a pharmaceutical composition for the prevention or treatment of inflammatory bowel disease, the composition containing the bispecific antibody having binding specificity to TNF-α and IFN-γ.

The inflammatory bowel disease may be one or more selected from the group consisting of Crohn's disease, ulcerative colitis, intestinal Behcet's disease, tuberculosis enteritis and diarrhea.

A pharmaceutically acceptable carrier contained in the pharmaceutical composition according to the present disclosure is commonly used in formulation. Examples of the carrier may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, and the like, but is not limited thereto. The pharmaceutical composition according to the present disclosure may additionally contain lubricants, wetting agents, sweetening agents, flavoring agents, emulsifying agents, suspending agents, preservatives, etc. in addition to the above ingredients. Suitable pharmaceutically acceptable carriers and formulations are described in detail in Remington's Pharmaceutical Sciences (latest edition). The pharmaceutical composition according to the present disclosure may be administered orally or parenterally. In the case of parenteral administration, intravenous injection, subcutaneous injection, intramuscular injection, intraperitoneal injection, endothelial administration, topical administration, intranasal administration, intrapulmonary administration, rectal administration, and the like may be used. When administered orally, the protein or peptide is digested. Thus, the oral composition should be coated with an active agent or be formulated to protect the composition from degradation in the stomach. Further, the pharmaceutical composition may be administered using any device capable of moving the active substance to the target cell.

The appropriate dosage of the pharmaceutical composition according to the present disclosure varies depending on factors such as formulation method, mode of administration, patient's age, weight, sex, pathological condition, food, administration time, route of administration, excretion rate and response sensitivity. Usually, the skilled physician may easily determine and prescribe the effective dosage for the desired treatment or prevention. According to a preferred embodiment of the present disclosure, the daily dose of the pharmaceutical composition according to the present disclosure may be 0.001 to 100 mg/kg. As used herein, the term "pharmaceutically effective amount" means an amount sufficient to prevent or treat the inflammatory bowel disease.

The pharmaceutical composition according to the present disclosure is formulated into a unit dosage form, using a pharmaceutically acceptable carrier and/or excipient and using a method that may be easily carried out by a person having ordinary knowledge in the technical field to which the present invention belongs. Alternatively, the pharmaceutical composition according to the present disclosure may be put into a multi-dosage container. In this connection, the formulation may be in the form of a solution, suspension or emulsion in an oil or aqueous medium, or in the form of an extract, powder, suppository, powdered drugs, granule, tablet or capsule. The formulation may additionally contain a dispersant or a stabilizer.

The antibody composition according to the present disclosure may be administered as an individual therapeutic agent or administered in combination with other therapeutic agents, and may be administered sequentially or simultaneously with a conventional therapeutic agent. The antibody may be used for the treatment of inflammatory bowel disease by injecting the antibody into the living body in the form of an antibody-therapeutic agent conjugate. The therapeutic agent may include chemotherapeutic agents, radionuclides, immunotherapeutic agents, cytokines, chemokines, toxins, biological agents, and enzyme inhibitors.

Hereinafter, the present disclosure will be described in more detail based on Examples. However, the following Examples are illustrative so that the present disclosure may be more easily understood, and the present disclosure is not limited to the Examples.

Example 1. Anti-TNF/IFN scFv-Fc Bispecific Antibody Expression Vector Construction To produce a bispecific antibody capable of conjugating simultaneously to TNF-α (tumor necrosis factor-alpha) and IFN-γ (interferon-gamma), which are cytokines that cause inflammatory bowel disease including Crohn's disease, we devised expression vectors as shown in FIG. 1.

As shown in FIG. 1, gene sequences in which the Fc domain of the antibody is fused to a single chain variable fragment (scFv) that may be conjugated to the two cytokines, respectively were designed. After optimizing codons for expression thereof in the CHO-DG44 cell line, genes were synthesized. The genes synthesized via the codon optimization were expressed as anti-TNF scFv-Fc (1497 bp, SEQ ID NO: 1) and anti-IFN scFv-Fc (1476 bp, SEQ ID NO: 2).

The synthesized anti-TNF scFv-Fc and anti-IFN scFv-Fc genes were identified using electrophoresis on an agarose gel. The results are shown in a) of FIG. 2. Next, the obtained genes were TA cloned into the pOptiVEC-TOPO vector to create the expression vectors which were named pOptiVEC/TNF and pOptiVEC/IFN, respectively. Each of the expression vectors was transformed into TOP10 *Escherichia coli* using a heat-shock method. The transformant was plated on S.O.C. medium (2% tryptone, 0.5% yeast extract, 10 mM NaCl, 2.5 mM KCl, 10 mM $MgCl_2$, 10 mM $MgSO_4$, and 20 mM glucose) containing ampicillin antibiotic. The transformant was cultured therein for 12 hours at 37° C. Then, colony PCR was performed to select the transformed *E. coli*. The results are shown in b) of FIG. 2.

Figure 2:
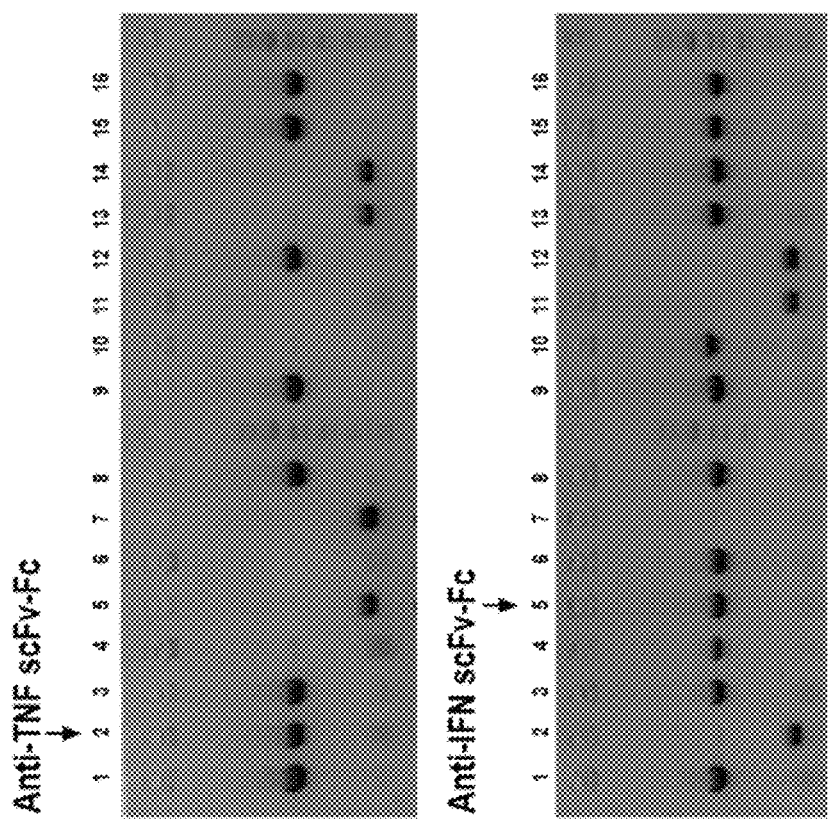
FIG. 2 is a diagram showing a result of identifying expressions of the synthesized anti-TNF scFv-Fc and anti-IFN scFv-Fc genes using electrophoresis on an agarose gel.
Figure 2:
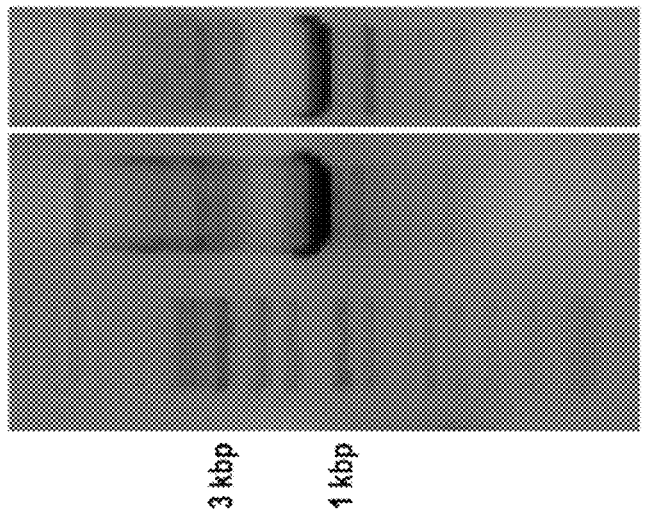

As shown in b) of FIG. 2, No. 2 and No. 5 *E. coli* clones which were identified as expressing each of the target genes were selected from the transformed *E. coli*. The vector was extracted therefrom. The selected vector is a vector capable of producing a bispecific antibody that may be conjugated to TNF-α and IFN-γ, and that may have the Fc domain fused thereto, thus realizing stability and easy purification.

Example 2. Transformation Using CHO-DG44 Cell Line and Production of Bispecific Antibody

2.1 Bispecific Antibody Expressing CHO Cell Line Production

Figure 3:
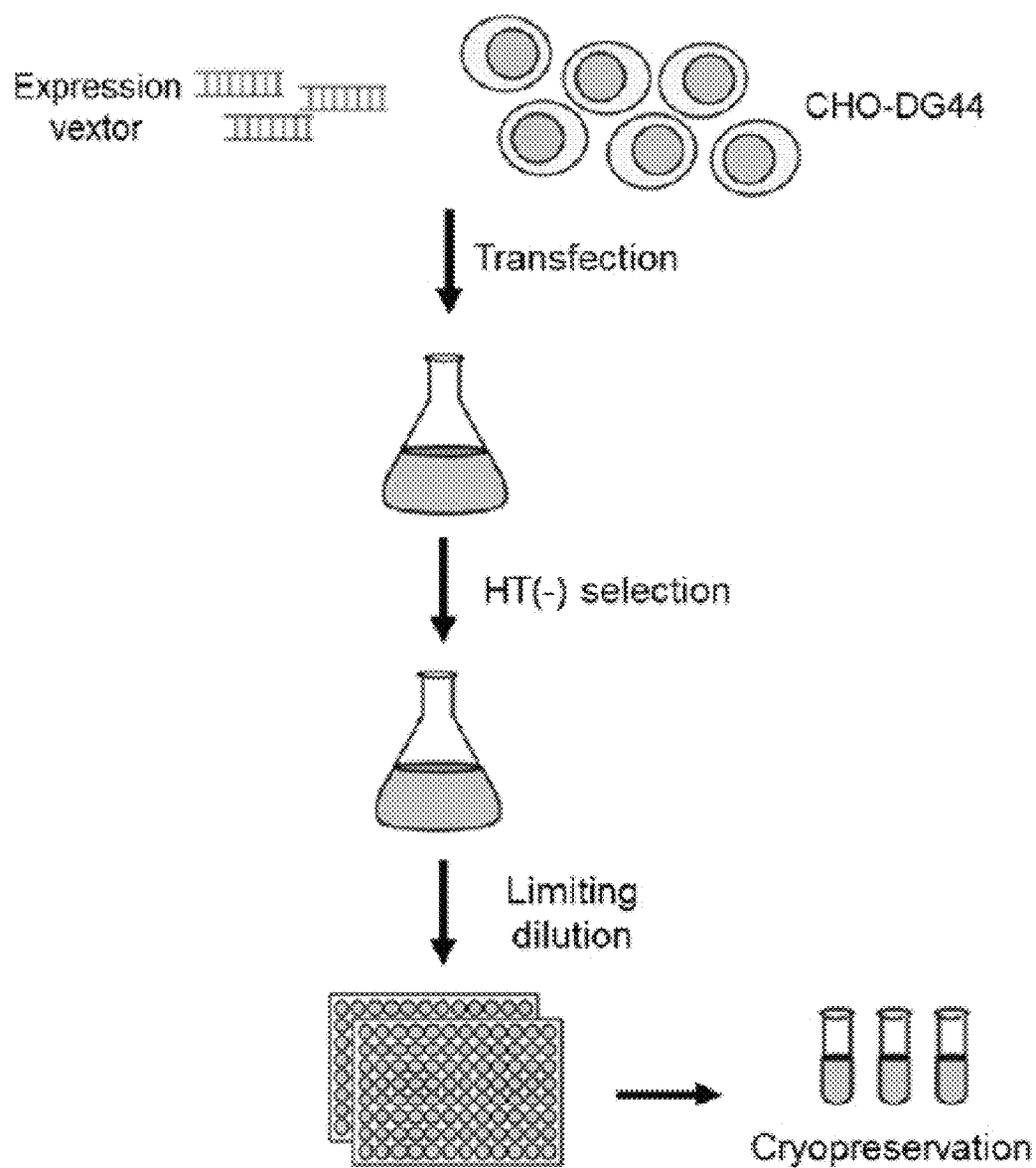
FIG. 3 is a schematic diagram showing a producing process of a cell line expressing a bispecific antibody.

In order to produce anti-TNF/IFN scFv-Fc bispecific antibodies, the two expression vectors prepared in Example 1 were simultaneously inserted into CHO-DG44 cells lacking the dihydrofolate reductase gene. Each of the pOptiVEC/TNF and pOptiVEC/IFN expression vectors was mixed with OptiPRO-SFM medium. Each mixture was added to Freestyle MAX reagent to prepare DNA-lipid complex. The formed complex was added to ProCHO5 medium containing 4 mM glutamine, and CHO cells at a concentration of $5 \times 10^5$ cells/mL were inoculated thereto. In order to establish a monoclonal cell line, the cells were cultured for 24 hours and then treated with 50 nM methotrexate to select a CHO cell line into which the target gene was introduced. The selected cells were cultured in a 96-well plate for 2 weeks using a limiting dilution method. The production process of the bispecific antibody-expressing CHO cell line is schematically shown in FIG. 3.

Figure 4:
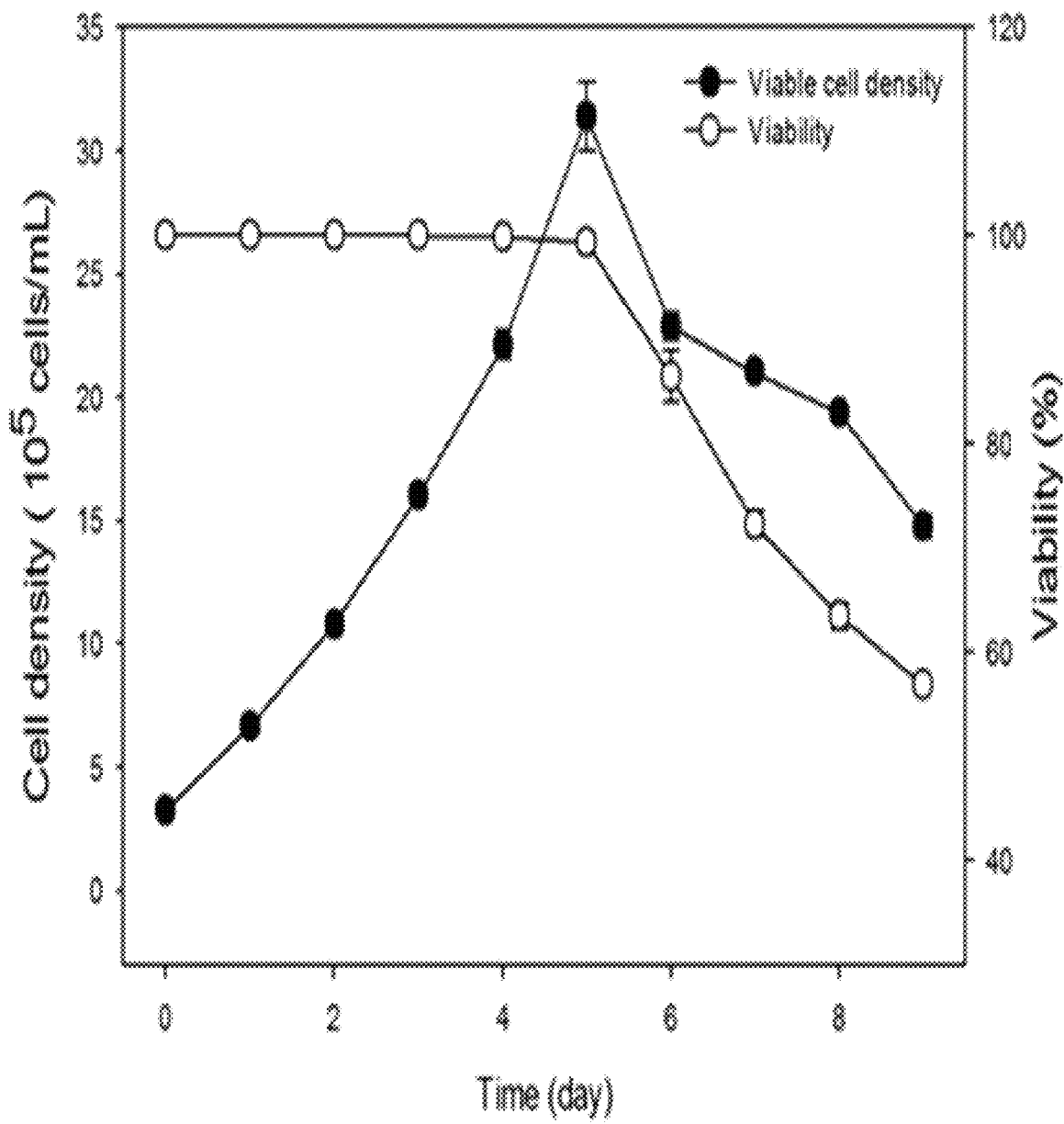
FIG. 4 is a diagram showing results of identifying cell density and cell viability of transformed CHO cells into which both pOptiVEC/TNF and pOptiVEC/IFN expression vectors are inserted.

The monoclonal transformants into which both pOptiVEC/TNF and pOptiVEC/IFN expression vectors were inserted were inoculated into ProCHO5 medium containing 4 mM glutamine at a concentration of $3 \times 10^5$ cells/mL, followed by suspension culture at 100 rpm. The prepared CHO cell line was batch cultured for 9 days and then cell growth and viability were analyzed. The results are shown in FIG. 4. The change in the production amount of the anti-TNF/IFN scFv-Fc bispecific antibody was measured using a sandwich enzyme linked immunosorbent assay (ELISA), and the results are shown in FIG. 5.

As shown in FIG. 4, the transformed CHO cell proliferated steadily until day 5. However, thereafter, rapid cell death occurred. On the 9th day of the culture, the cell viability decreased to 60% or less.

Figure 5:
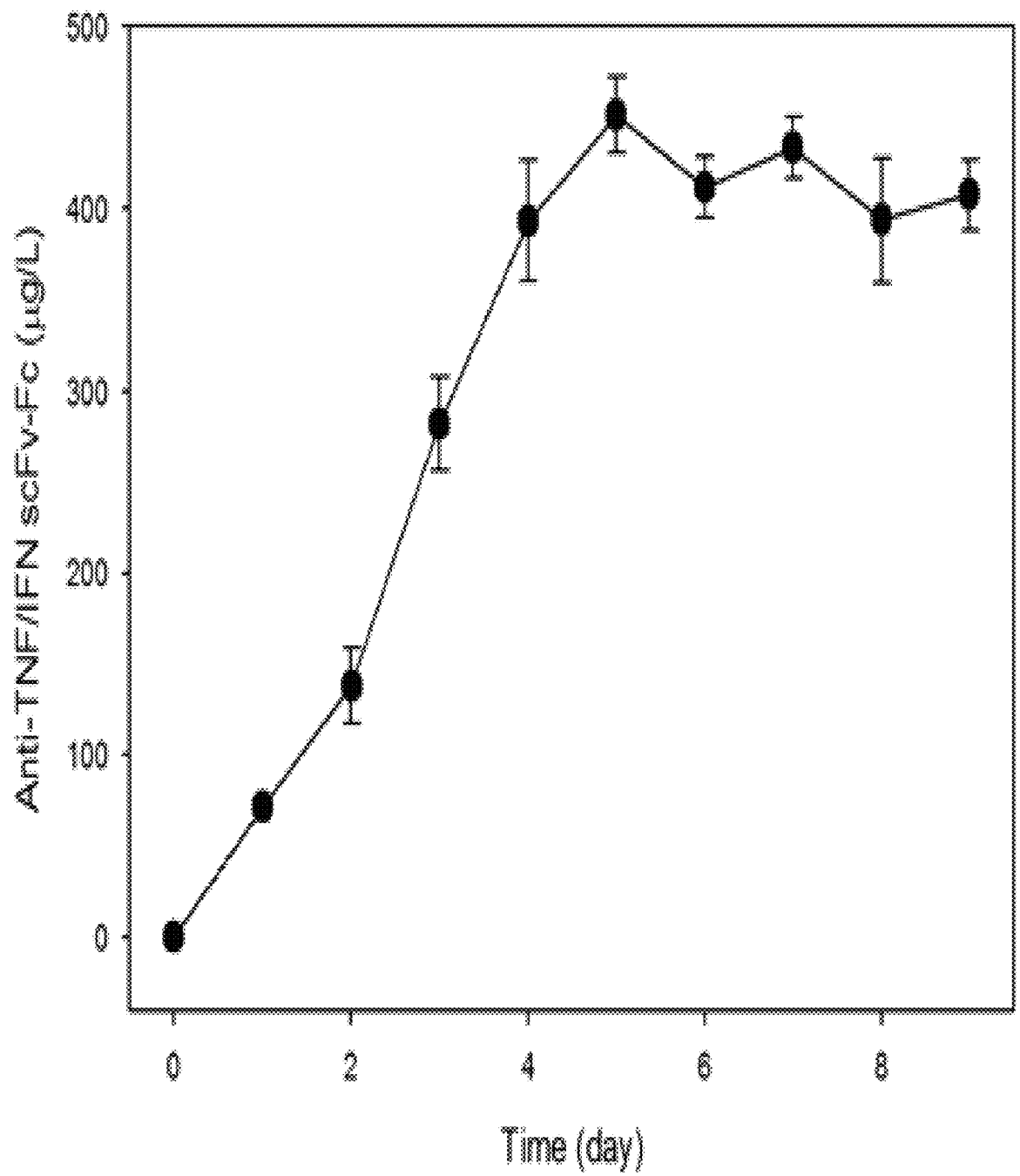
FIG. 5 is a diagram showing a result of identifying the expression of the anti-TNF/IFN scFv-Fc bispecific antibody.

As shown in FIG. 5, it was identified that the bispecific antibody was expressed at a concentration of 400 mg/L or more.

Figure 6:
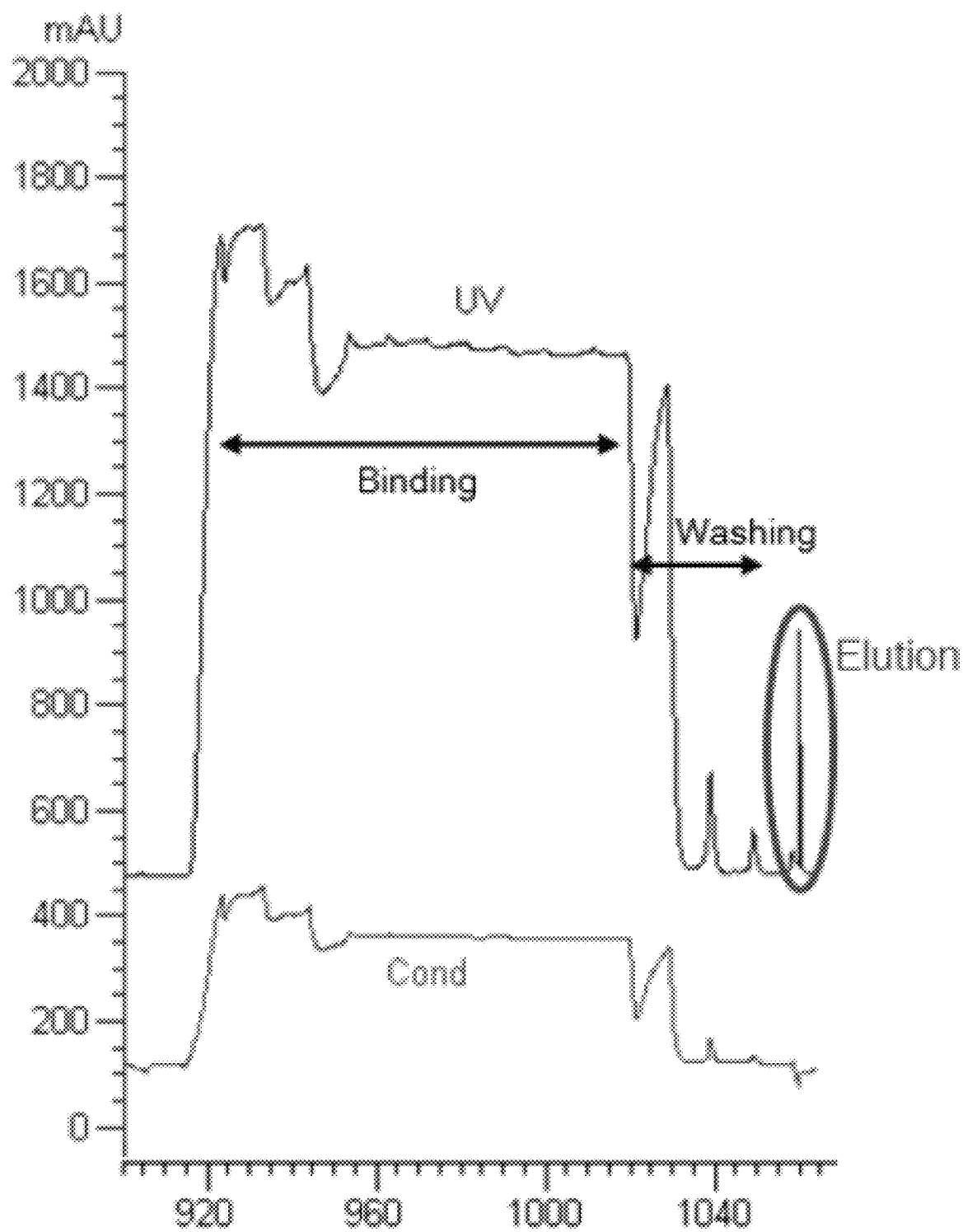
FIG. 6 is a diagram showing a result of purification of the bispecific antibody as purified using a Protein A purification method.

2.2 Purification and Expression Identification of Produced Bispecific Antibodies A HiTrap Protein A column was used to purify the anti-TNF/IFN scFv-Fc bispecific antibody expressed in the medium after culturing the transformed CHO cells. After mixing the culture solution with 20 mM sodium phosphate buffer, the mixture was bound to the resin. 20 mM sodium phosphate buffer was poured onto the column for washing. Thereafter, the peak detected at UV 260 nm wavelength using 0.1 M citric acid elution buffer was identified, and then the anti-TNF/IFN scFv-Fc bispecific antibody was isolated therefrom. FIG. 6 shows the results of purification of the bispecific antibody as purified using the Protein A purification method.

The purified bispecific antibody was separated from a 10% SDS-PAGE gel, and was stained with Coomassie blue solution to measure the molecular weight thereof. After electrophoresis thereof on a gel for Western Blot analysis, the antibody was transferred to a nitrocellulose membrane. The expression of the bispecific antibody was identified using goat anti-human IgG Fc and rabbit anti-goat IgG as primary and secondary antibodies, respectively. The results are shown in FIG. 7.

Figure 7:
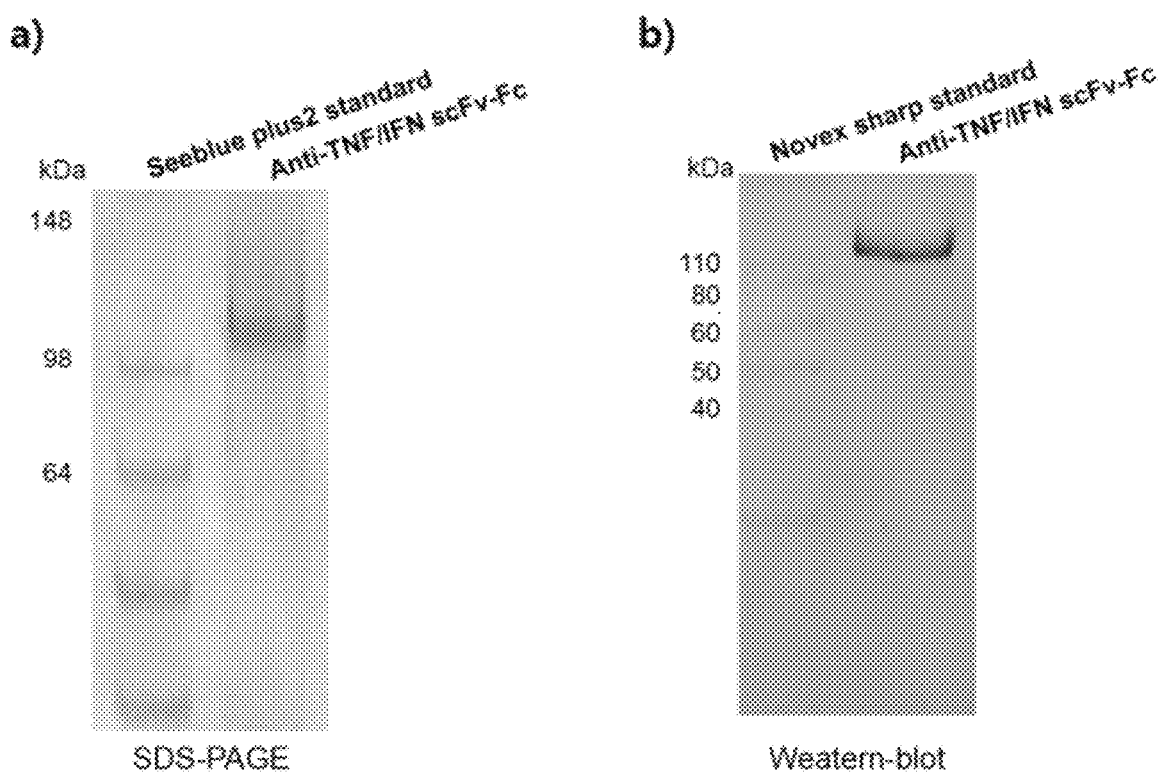
FIG. 7 is a diagram showing a result of identifying the expression and molecular weight of the purified bispecific antibody via SDS-PAGE (a) and Western blot (b).

As shown in a) of FIG. 7 and b) of FIG. 7, the produced bispecific antibody was identified as having a molecular weight of 110 kDa. Expression of the antibody was clearly identified using SDS-PAGE and Western blot.

Figure 8:
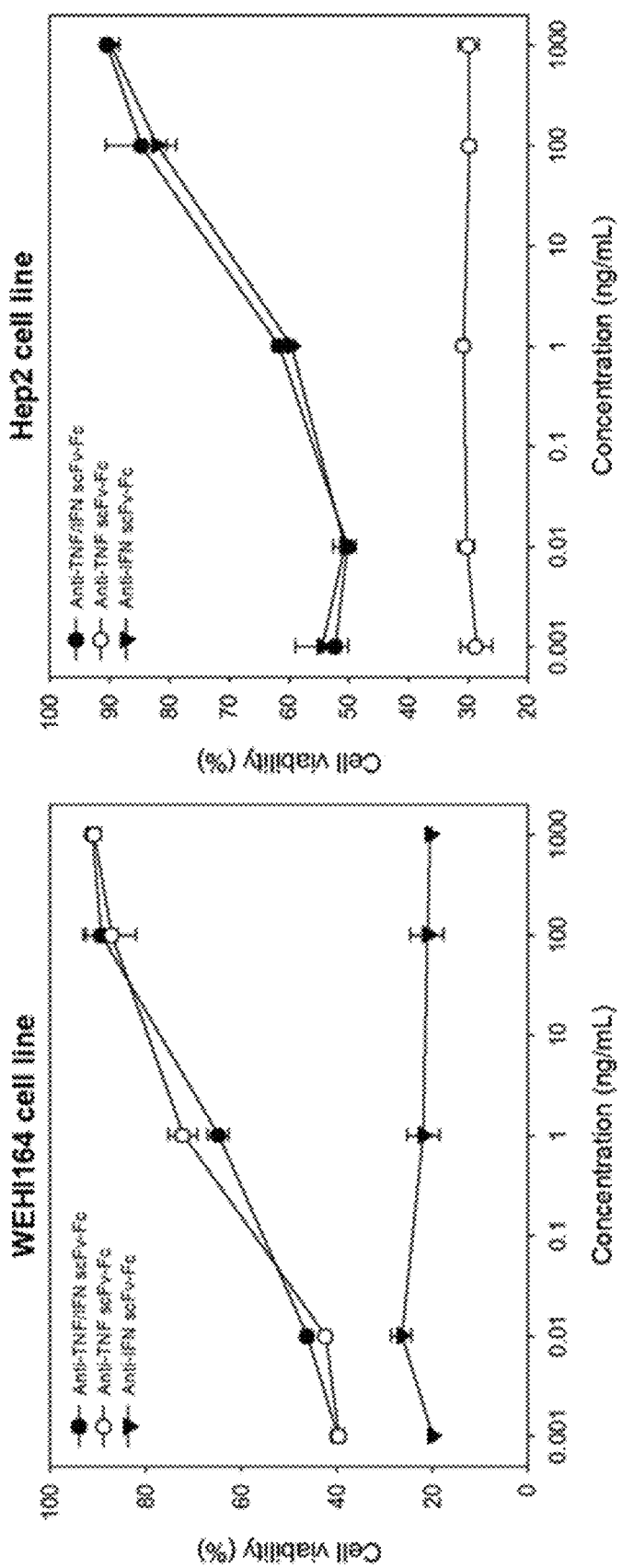
FIG. 8 shows a result of identifying the binding ability of anti-TNF/IFN scFv-Fc bispecific antibody to TNF-α and IFN-γ based on changes in cell viability of WEHI164 cells and Hep2 cell lines based on presences of anti-TNF/IFN scFv-Fc bispecific antibody, anti-TNF scFv-Fc single antibody, and anti-IFN scFv-Fc single antibody.

Example 3. Evaluation of Binding Ability of Bispecific Antibody Using WEHI164 and Hep2 Cell Line In order to evaluate whether the anti-TNF/IFN scFv-Fc bispecific antibody may conjugate to two types of antigens at the same time, the evaluation of binding capacity was performed using WEHI164 and Hep2 cell lines. The both cell lines are characterized by inhibition of growth due to treatment thereof with TNF-α and IFN-γ, respectively. Therefore, TNF-α was added to the medium for culturing the WEHI164 cells. The purified bispecific antibody and each single antibody (anti-TNF scFv-Fc, and anti-IFN scFv-Fc) were diluted step by step. Then, each diluted antibody was applied to the cells. FIG. 8 shows the results of identifying cell viability due to the antibody treatment.

As shown in FIG. 8, it was identified that when each of anti-TNF/IFN scFv-Fc and anti-TNF scFv-Fc antibodies was present in the medium, the proliferation of WEHI164 cells was maintained due to binding thereof to TNF-α. During the culture of the Hep2 cells, under IFN-γ-treated condition, the anti-TNF scFv-Fc antibody was unable to conjugate with the antigen, thereby inhibiting cell growth.

Thus, it was proved that the bispecific antibody produced in the transformed CHO cell conjugated to both TNF-α and IFN-γ. This indicates that the novel bispecific antibody developed according to the present disclosure may conjugate to TNF-α and IFN-γ as the causes of inflammatory bowel disease to suppress the same and thus may be used for the treatment of inflammatory bowel disease.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A polynucleotide encoding a bispecific antibody having binding specificity to TNF-α and IFN-γ, the polynucleotide comprising the nucleotide sequence of SEQ ID NO: 1 encoding anti-TNF scFv-Fc and the nucleotide sequence of SEQ ID NO: 2 encoding anti-IFN scFv-Fc.

2. A bispecific antibody having binding specificity to TNF-α and IFN-γ, the bispecific antibody containing anti-TNF scFv-Fc having the sequence of SEQ ID NO: 3 and anti-IFN scFv-Fc having the sequence of SEQ ID NO: 4.

3. A polynucleotide encoding a bispecific antibody having binding specificity to TNF-α and IFN-γ, wherein the polynucleotide encodes the bispecific antibody of claim 2.

4. A recombinant expression vector containing the polynucleotide of claim 1.

5. A recombinant expression vector containing the polynucleotide of claim 3.

6. A host cell transformed using the vector of claim 4.

7. A host cell transformed using the vector of claim 5.

8. The host cell of claim 6, wherein the host cell is selected from the group consisting of animal cells, plant cells, yeast, *E. coli*, and insect cells.

9. The host cell of claim 7, wherein the host cell is selected from theft group consisting of animal cells, plant cells, yeast, *E. coli*, and insect cells.

10. A method for preparing a bispecific antibody having binding specificity to TNF-α and IFN-γ, the method comprising:
    1) Preparing a transformant by introducing a vector comprising the nucleotide sequence of SEQ ID NO: 1 encoding an anti-TNF scFv-Fc and the nucleotide sequence of SEQ ID NO: 2 encoding an anti-IFN scFv-Fc into a host cell; and
    2) Culturing the transformant in a medium and then separating and purifying an anti-TNF/IFN scFv-Fc bispecific antibody expressed in the medium.

11. The method of claim 10, wherein the separation and purification in 2) is performed while targeting an Fc domain.

12. A bispecific antibody having binding specificity to TNF-α and IFN-γ, the antibody being prepared by the preparation method of claim 10.

13. The bispecific antibody of claim 12, wherein the bispecific antibody contains anti-TNF scFv-Fc represented by SEQ ID NO: 3 and anti-IFN scFv-Fc represented by SEQ ID NO: 4.

14. A pharmaceutical composition for treatment of inflammatory bowel disease, the composition containing the bispecific antibody of claim 12.

15. A pharmaceutical composition for treatment of inflammatory bowel disease, the composition containing the bispecific antibody of claim 13.

16. The pharmaceutical composition of claim 14, wherein the inflammatory bowel disease is at least one selected from a group consisting of Crohn's disease, ulcerative colitis, intestinal Behcet's disease, tuberculosis enteritis and diarrhea.

17. The pharmaceutical composition of claim 15, wherein the inflammatory bowel disease is at least one selected from a group consisting of Crohn's disease, ulcerative colitis, intestinal Behcet's disease, tuberculosis enteritis and diarrhea.

* * * * *

SEQUENCE LISTING

```
<160> NUMBER OF SEQ ID NOS: 4

<210> SEQ ID NO 1
<211> LENGTH: 1497
<212> TYPE: DNA
<213> ORGANISM: Artificial Sequence
<220> FEATURE:
<223> OTHER INFORMATION: Anti-TNF scFv-Fc

<400> SEQUENCE: 1
```

```
atggagaccg acaccctgct gctgtgggtg ctgctgctgt gggtgcccgg cagcaccggc    60
gacatggccg aggtgcagct gctggagagc ggcggcggcc tggtgcagcc cggcggcagc   120
ctgagactga gctgcgccgc cagcggcttc accttcagca gctacgccat gagctgggtg   180
agacaggccc ccggcaaggg cctggagtgg gtgagcagca tcagcagcac cggcgccagc   240
accacctacg ccgacagcgt gaagggcaga ttcaccatca gcagagacaa cagcaagaac   300
accctgtacc tgcagatgaa cagcctgaga gccgaggaca ccgccgtgta ctactgcgcc   360
aagggcggcg ccgccttcga ctactggggc cagggcaccc tggtgaccgt gagcagcggc   420
ggcggcggca gcggcggcgg cggcagcggc ggcggcggca gcaccgacat ccagatgacc   480
cagagcccca gcagcctgag cgccagcgtg ggcgacagag tgaccatcac ctgcagagcc   540
agccagagca tcagcagcta cctgaactgg taccagcaga agcccggcaa ggcccccaag   600
ctgctgatct acagcgccag ctacctgcag agcggcgtgc ccagcagatt cagcggcagc   660
ggcagcggca ccgacttcac cctgaccatc agcagcctgc agcccgagga cttcgccacc   720
tactactgcc agcaggccaa caacgccccc accaccttcg gccagggcac caaggtggag   780
atcaagagag ccgccgccga gcccaagagc tgcgacaaga cccacacctg cccccccctgc   840 cccgccccccg agctgctggg cggccccagc gtgttcctgt tcccccccaa gcccaaggac   900
accctgatga tcagcagaac ccccggcgtg acctgcgtgg tggtggacgt gagccacgag   960
gaccccgagg tgaagttcaa ctggtacgtg gacggcgtgg aggtgcacaa cgccaagacc   1020
aagcccagag aggagcagta caacagcacc tacagagtgg tgagcgtgct gaccgtgctg   1080
caccaggact ggctgaacgg caaggagtac aagtgcaagg tgagcaacaa ggccctgccc   1140
gcccccatcg agaagaccat cagcaaggcc aagggccagc ccagagagcc ccaggtgtac   1200
accctgcccc ccagcagaga cgagctgacc aagaaccagg tgagcctgac ctgcctggtg   1260
aagggcttct accccagcga catcgccgtg gagtgggaga gcaacggcca gcccgagaac   1320
aactacaaga ccacccccccc cgtgctggac agcgacggca gcttcttcct gtacagcaag   1380
ctgaccgtgg acaagagcag atggcagcag ggcaacgtgt tcagctgcag cgtgatgcac   1440
gaggccctgc acaaccacta cacccagaag agcctgagcc tgagccccgg caagtga     1497
```

<210> SEQ ID NO 2
<211> LENGTH: 1476
<212> TYPE: DNA
<213> ORGANISM: Artificial Sequence
<220> FEATURE:
<223> OTHER INFORMATION: Anti-IFN scFv-Fc

<400> SEQUENCE: 2

```
atggagaccg acaccctgct gctgtgggtg ctgctgctgt gggtgcccgg cagcaccggc    60
gacgaggtgc agctgctgga gagcggcggc ggcctggtgc agcccggcgg cagcctgaga   120
ctgagctgcg ccgccagcgg cttcaccttc agcagctacg ccatgagctg ggtgagacag   180 gccccccggca agggcctgga gtgggtgagc gccatcagcg gcagcggcgg cagcacctac   240
tacgccgaca gcgtgaaggg cagattcacc atcagcagag acaacagcaa gaacaccctg   300
tacctgcaga tgaacagcct gagagccgag gacaccgccg tgtactactg cgccaagaga   360 gccccccgcct tcgactactg gggccagggc accctggtga ccgtgagcag cggcgacggc   420
agcagcggcg gcagcggcgg cgccagcacc ggcgagatcg tgctgaccca gagccccggc   480
accctgagcc tgagccccgg cgagagagcc accctgagct gcagagccag ccagagcgtg   540
```

-continued

```
agcagcagct acctggcctg gtaccagcag aagcccggcc aggcccccag actgctgatc    600
tacggcgcca gcagcagagc caccggcatc cccgacagat tcagcggcag cggcagcggc    660
accgacttca ccctgaccat cagcagactg agcccgagg  acttcgccgt gtactactgc    720
cagcagatgg gcgacagccc caccaccttc ggccagggca ccaaggtgga gatcaaggag    780
cccaagagct gcgacaagac ccacacctgc cccccctgcc ccgcccccga gctgctgggc    840
ggccccagcg tgttcctgtt cccccccaag cccaaggaca ccctgatgat cagcagaacc    900
cccggcgtga cctgcgtggt ggtggacgtg agccacgagg accccgaggt gaagttcaac    960
tggtacgtgg acggcgtgga ggtgcacaac gccaagacca gcccagaga ggagcagtac    1020
aacagcacct acagagtggt gagcgtgctg accgtgctgc accaggactg gctgaacggc    1080
aaggagtaca agtgcaaggt gagcaacaag gccctgcccg cccccatcga aagaccatc    1140
agcaaggcca agggccagcc cagagagccc caggtgtaca ccctgccccc cagcagagac    1200
gagctgacca gaaccaggt  gagcctgacc tgcctggtga agggcttcta ccccagcgac    1260
atcgccgtgg agtgggagag caacggccag cccgagaaca actacaagac cacccccccc    1320
gtgctggaca gcgacggcag cttcttcctg tacagcaagc tgaccgtgga caagagcaga    1380
tggcagcagg gcaacgtgtt cagctgcagc gtgatgcacg aggccctgca caaccactac    1440
acccagaaga gcctgagcct gagccccggc aagtga                              1476
```

<210> SEQ ID NO 3
<211> LENGTH: 497
<212> TYPE: PRT
<213> ORGANISM: Artificial Sequence
<220> FEATURE:
<223> OTHER INFORMATION: Anti-TNF scFv-Fc

<400> SEQUENCE: 3

```
Met Glu Thr Asp Thr Leu Leu Leu Trp Val Leu Leu Leu Trp Val Pro
1               5                   10                  15

Gly Ser Thr Gly Met Ala Glu Val Gln Leu Leu Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ser Ser Ile Ser Ser Thr Gly Ala Ser Thr
65                  70                  75                  80

Thr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Lys Gly Gly Ala Ala Phe Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Thr Asp Ile Gln Met Thr Gln
145                 150                 155                 160

Ser Pro Ser Ser Leu Ser Ala Ser Val Gly Asp Arg Val Thr Ile Thr
                165                 170                 175

Cys Arg Ala Ser Gln Ser Ile Ser Ser Tyr Leu Asn Trp Tyr Gln Gln
            180                 185                 190

Lys Pro Gly Lys Ala Pro Lys Leu Leu Ile Tyr Ser Ala Ser Tyr Leu
```

-continued

```
        195                 200                 205

Gln Ser Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Gln Gln Ala Asn Asn Ala Pro Thr Thr Phe Gly Gln Gly Thr
                245                 250                 255

Lys Val Glu Ile Lys Arg Ala Ala Ala Glu Pro Lys Ser Cys Asp Lys
            260                 265                 270

Thr His Thr Cys Pro Pro Cys Pro Ala Pro Glu Leu Leu Gly Gly Pro
        275                 280                 285

Ser Val Phe Leu Phe Pro Pro Lys Pro Lys Asp Thr Leu Met Ile Ser
    290                 295                 300

Arg Thr Pro Gly Val Thr Cys Val Val Val Asp Val Ser His Glu Asp
305                 310                 315                 320

Pro Glu Val Lys Phe Asn Trp Tyr Val Asp Gly Val Glu Val His Asn
                325                 330                 335

Ala Lys Thr Lys Pro Arg Glu Glu Gln Tyr Asn Ser Thr Tyr Arg Val
            340                 345                 350

Val Ser Val Leu Thr Val Leu His Gln Asp Trp Leu Asn Gly Lys Glu
        355                 360                 365

Tyr Lys Cys Lys Val Ser Asn Lys Ala Leu Pro Ala Pro Ile Glu Lys
    370                 375                 380

Thr Ile Ser Lys Ala Lys Gly Gln Pro Arg Glu Pro Gln Val Tyr Thr
385                 390                 395                 400

Leu Pro Pro Ser Arg Asp Glu Leu Thr Lys Asn Gln Val Ser Leu Thr
                405                 410                 415

Cys Leu Val Lys Gly Phe Tyr Pro Ser Asp Ile Ala Val Glu Trp Glu
            420                 425                 430

Ser Asn Gly Gln Pro Glu Asn Asn Tyr Lys Thr Thr Pro Pro Val Leu
        435                 440                 445

Asp Ser Asp Gly Ser Phe Phe Leu Tyr Ser Lys Leu Thr Val Asp Lys
    450                 455                 460

Ser Arg Trp Gln Gln Gly Asn Val Phe Ser Cys Ser Val Met His Glu
465                 470                 475                 480

Ala Leu His Asn His Tyr Thr Gln Lys Ser Leu Ser Leu Ser Pro Gly
                485                 490                 495

Lys
```

<210> SEQ ID NO 4
<211> LENGTH: 490
<212> TYPE: PRT
<213> ORGANISM: Artificial Sequence
<220> FEATURE:
<223> OTHER INFORMATION: Anti-IFN scFv-Fc

<400> SEQUENCE: 4
```
Met Glu Thr Asp Thr Leu Leu Leu Trp Val Leu Leu Leu Trp Val Pro
1               5                   10                  15

Gly Ser Thr Gly Glu Val Gln Leu Leu Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Ser Tyr Ala Met Ser Trp Val Arg Gln Ala Pro Gly Lys Gly
    50                  55                  60
```

```
Leu Glu Trp Val Ser Ala Ile Ser Gly Ser Gly Gly Ser Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Lys Arg Ala Pro Ala Phe Asp Tyr Trp Gly Gln
        115                 120                 125

Gly Thr Leu Val Thr Val Ser Ser Gly Asp Gly Ser Ser Gly Gly Ser
    130                 135                 140

Gly Gly Ala Ser Thr Gly Glu Ile Val Leu Thr Gln Ser Pro Gly Thr
145                 150                 155                 160

Leu Ser Leu Ser Pro Gly Glu Arg Ala Thr Leu Ser Cys Arg Ala Ser
                165                 170                 175

Gln Ser Val Ser Ser Ser Tyr Leu Ala Trp Tyr Gln Gln Lys Pro Gly
            180                 185                 190

Gln Ala Pro Arg Leu Leu Ile Tyr Gly Ala Ser Ser Arg Ala Thr Gly
        195                 200                 205

Ile Pro Asp Arg Phe Ser Gly Ser Gly Ser Gly Thr Asp Phe Thr Leu
    210                 215                 220

Thr Ile Ser Arg Leu Glu Pro Glu Asp Phe Ala Val Tyr Tyr Cys Gln
225                 230                 235                 240

Gln Met Gly Asp Ser Pro Thr Thr Phe Gly Gln Gly Thr Lys Val Glu
                245                 250                 255

Ile Lys Glu Pro Lys Ser Cys Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Gly Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445
```

-continued

```
Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465             470                 475                 480

Gln Lys Ser Leu Ser Leu Ser Pro Gly Lys
                485             490
```